US005295982A

United States Patent [19]

Schatz

[11] Patent Number: 5,295,982

[45] Date of Patent: Mar. 22, 1994

[54] SUCTION DEVICE FOR CLEANING SKIN

[76] Inventor: Viktor Schatz, Birkenweg 2, 5900 Siegen, Fed. Rep. of Germany

[21] Appl. No.: 758,769

[22] Filed: Sep. 12, 1991

[30] Foreign Application Priority Data

Sep. 15, 1990 [DE] Fed. Rep. of Germany ....... 4029326

[51] Int. Cl.[5] ............ A61M 1/00

[52] U.S. Cl. ............ 604/313; 604/315

[58] Field of Search ............ 604/313, 315; 128/39, 128/40, 32; 137/859

[56] References Cited

U.S. PATENT DOCUMENTS

| | | | |
|---|---|---|---|
| 722,019 | 3/1903 | Hildebrandt et al. | 604/315 |
| 948,005 | 2/1910 | Campbell | 604/315 |
| 1,141,373 | 6/1915 | Behm | 604/315 |
| 1,225,244 | 6/1917 | Hendricks | 604/315 |
| 1,291,290 | 1/1919 | Veomett | 128/32 |
| 2,571,398 | 10/1951 | Wheeler | 128/40 R |
| 3,794,035 | 2/1974 | Brenner . | |
| 4,141,379 | 2/1979 | Manske | 137/859 |
| 4,292,971 | 10/1981 | Smit et al. . | |
| 4,609,368 | 9/1986 | Dotson, Jr. . | |
| 4,765,316 | 8/1988 | Marshall | 128/39 |
| 4,900,316 | 2/1990 | Yamamoto . | |

FOREIGN PATENT DOCUMENTS

| | | |
|---|---|---|
| 2611721 | 9/1977 | Fed. Rep. of Germany . |
| 2626179 | 7/1989 | France . |

*Primary Examiner*—David Isabella
*Assistant Examiner*—Rob Clarke
*Attorney, Agent, or Firm*—Anderson Kill Olick & Oshinsky

[57] ABSTRACT

A suction device for cleaning skin having a suction nozzle with a plurality of openings that are covered by an elastic diaphragm which is drawn into the openings by a pulsating drive force so that the diaphragm forms a plurality of pulsating secondary vacuum pumps in contact with the skin, thus, the vacuum action on the skin is divided into short variable suction pulses and the covering elastic diaphragm offers an easily exchangeable disposable hygienic protection.

15 Claims, 3 Drawing Sheets

SUCTION DEVICE FOR CLEANING SKIN

BACKGROUND OF THE INVENTION

The invention is directed to a device for cleaning deep into the pores of the skin according to mechanical principles.

The care of the skin holds an important place in society and represents an extremely large and competitive market. Thus, a great many methods have been invented and implemented, namely, cosmetic masks and ointments, treatments with water, steam and also mechanical suction devices.

The advantage of cosmetic means is their favorable chemical-biological effect on the skin cells, but disadvantages reside in the relatively great expenditure of time for mask treatments, as well as in the problem of reaching deeper skin layers.

Steam treatment requires special equipment and therefore likewise requires a time-consuming treatment in cosmetics practices.

In order to achieve the best possible effect in the use of cosmetic ointments it is advisable to clean the skin thoroughly beforehand and remove hardened deposits in the pores.

Treatment methods with mechanical suction devices are described in the patent literature, e.g., in FR 26 26 179 A, U.S. Pat. No. 4,900,316 and U.S. Pat. No. 2,794,035, and concern typical known devices for cleaning the skin with a vacuum pump (FR 26 26 179 A), a suction bell (U.S. Pat. No. 4,900,316) or a suction nozzle (U.S. Pat. No. 3,794,035) which are placed on the skin and comprise a connection hose between the pump and the suction bell or nozzle. In so doing, steam action and pulsating suction can also be provided, as is described in U.S. Pat. No. 4,292,971. In this case, the pulsating operation serves for alternating between steam action and vacuum action on the one hand and for a massaging action on the skin on the other hand.

Overlapping treatment by means of ultrasonic waves is suggested for opening the pores. In this case, U.S. Pat. No. 4,609,368 describes a microsurgical suction handpiece with an ultrasonic source which causes a reduction in size of the tissue parts to be sucked out. This treatment has nothing to do with skin cleaning. In this instance, the use of ultrasonics serves for loosening and reducing the size of body tissue.

DE 26 11 721 B2 discloses a medical suction device for sucking tissue serum; suction device can be placed on the skin of a patient, its suction opening being covered by a tightly meshed sieve, wherein a holder for previously prepared fleece paper, containing a supporting sieve for the fleece paper, is provided behind the sieve. The skin is accordingly prevented from being sucked into the suction opening too vigorously, and the veins of the patient, which must be kept healthy for infusions which may be necessary later are treated with care. This medical device also has nothing to do with skin cleaning.

The technical problem in all known treatment methods for skin cleaning with suction devices is the risk of blood effusions and blood clots as a result of sucking blood from the capillary vessels in the upper layers of the skin, so that the skin can suffer permanent discoloration. Moreover, such devices must be very carefully cleaned or sterilized in order to prevent the transmission of skin diseases, or relatively expensive disposable tools must be used, since the suctioned skin deposits unavoidably soil the interior of the suction ducts.

SUMMARY OF THE INVENTION

Accordingly, it is an object of the present invention to provide a technical solution for effectively freeing the skin of pore impurities and pimples over a large surface area or, if necessary, locally, and in so doing to safely prevent the risk of blood effusion and to ensure hygienic protection which is simple to use.

Pursuant to this object, and others which will become apparent hereafter, one aspect of the present invention resides in a suction nozzle of a suction device for cleaning the skin; suction nozzle has a plurality of openings which are covered by an elastic diaphragm which is drawn into the openings by means of a pulsating drive force in such a way that the diaphragm forms a plurality of pulsating, secondary vacuum pumps in contact with the skin. Possible blood effusions are effectively prevented by means of the manner in which the vacuum action on the skin and skin pores is divided up into short suction pulses. Since the individual suction pulse is limited with respect to its duration and is adapted to the skin type, it does not matter how long the user allows the device to act on the skin.

In a further embodiment of the invention, the pulsating drive force is generated by a vacuum pump. The suction openings of the suction nozzle are covered by a common cap of elastic material so as to achieve the distribution of pressure and vacuum pressure along a plurality of suction openings connected to the vacuum pump and simultaneously to protect the interior of the vacuum chamber from the penetration of dirt and to offer an easily exchangeable disposable hygienic protection, which can also be conveniently cleaned, if necessary.

Further, as an alternative to a drive produced by means of a vacuum pump, the pulsating drive force produced by means of electromagnets and the elastic diaphragm contain fine inserts or a layer of magnetic material which, when attracted by one or more electromagnets, draw the diaphragm into the suction opening. In so doing, a mini-vacuum pump acting on the skin and the skin pores is formed in the same manner in every suction opening.

The pulse parameters of the pulsating drive force are controlled and applied in such a way that an adaptation to different skin types is ensured by means of varying the height and width, as well as the edge steepness, mark-space ratio and other parameters, wherein the invention is based on the idea of providing a tool for the precise controlling and limiting of quantities which are difficult to meter, by means of dividing these quantities into short pulses.

In another advantageous embodiment of the invention, the openings of the suction nozzle are formed by means of a plurality of offset grids which are then covered by the elastic diaphragm.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF PREFERRED EMBODIMENTS

Figure 1:
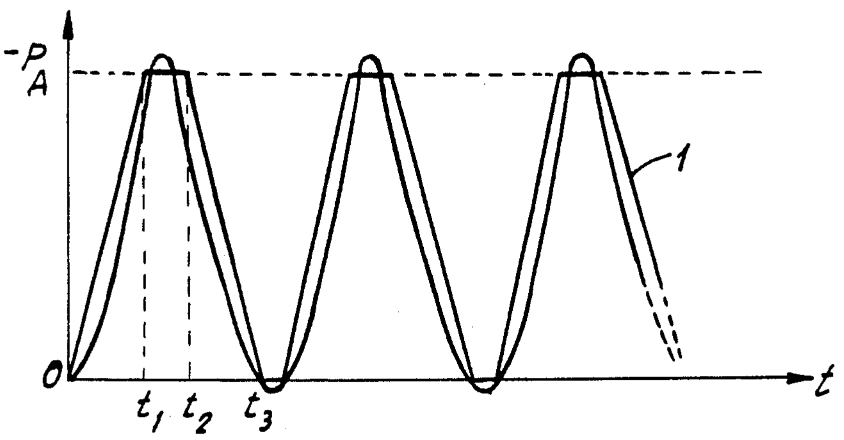
FIG. 1 shows the suction pulses illustrated by an idealized characteristic line.

FIG. 1 illustrates suction pulses as an embodiment example by means of an idealized characteristic line 1. The propagation of the vacuum wave in the inner skin layers is effected in a continuous manner with respect to time according to a time-dependent fuction, wherein a determined depth can be adjusted in the selected area by changing the pulse parameters described previously.

Figure 2:
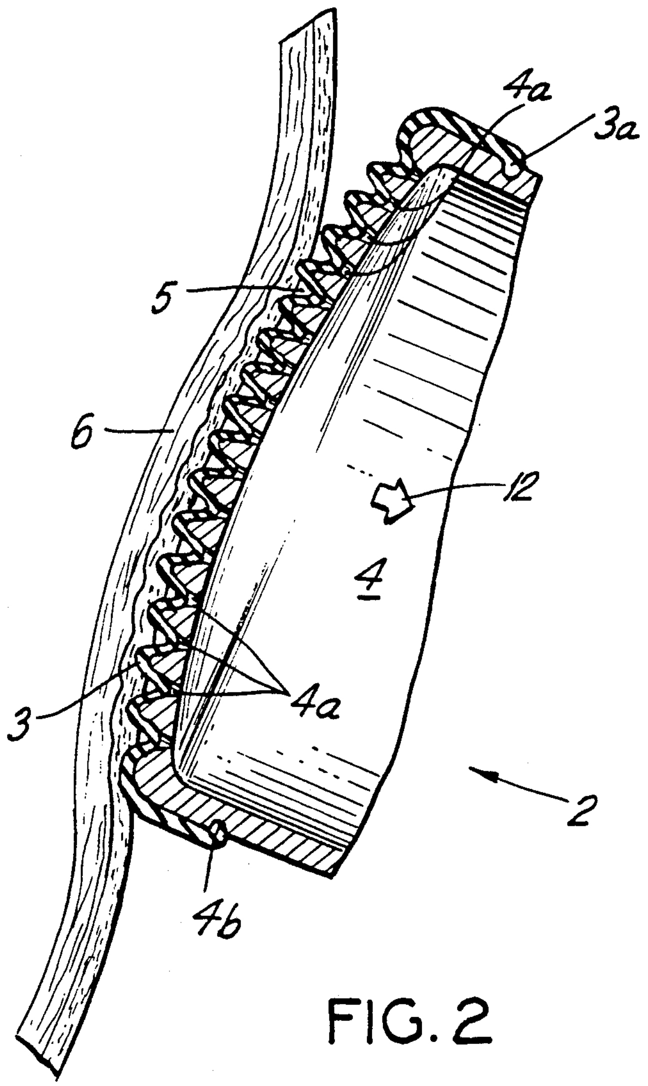
FIG. 2 shows the suction nozzle with elastic diaphragm and vacuum drive of the present invention.

FIG. 2 shows an embodiment of the suction device 2, in which the suction vacuum of the vacuum pump (not shown) first acts on the elastic diaphragm 3, wherein the diaphragm, which is sucked into the many openings 4*a* of the suction nozzle 4, in turn forms an equal number of secondary mini-vacuum pumps 5 which act on the skin 6 and on the skin pores 7. The diaphragm 3 has a bead edge 3*a* that sealingly engages in a groove 4*b* provided in the circumferential surface of the suction nozzle 4. Thus, the diaphragm 3 forms a cap for the suction nozzle 4. The deposits which are carried from the skin pores 7 to the surface are uniformly distributed on the surface of the skin 6 and the rubber diaphragm 3 in a simple manner and can be removed subsequently with a cleaning cloth. There are zones of normal pressure or slight vacuum pressure between the suction pulses, wherein the diaphragm 3 is tensioned and/or lifted along the suction openings 4*a* under the influence of inherent elastic forces and/or the pressing force of the air. The skin 6 is relaxed in the meantime and the possible excess quantity of exiting air can escape via lateral ducts or openings (not shown) in the rubber diaphragm 3 which are provided for this purpose.

Figure 5:
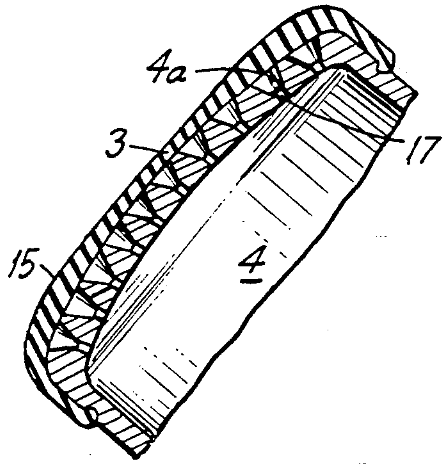
FIG. 5 shows a diaphragm having a thickness which increases toward the edge.
Figure 6:
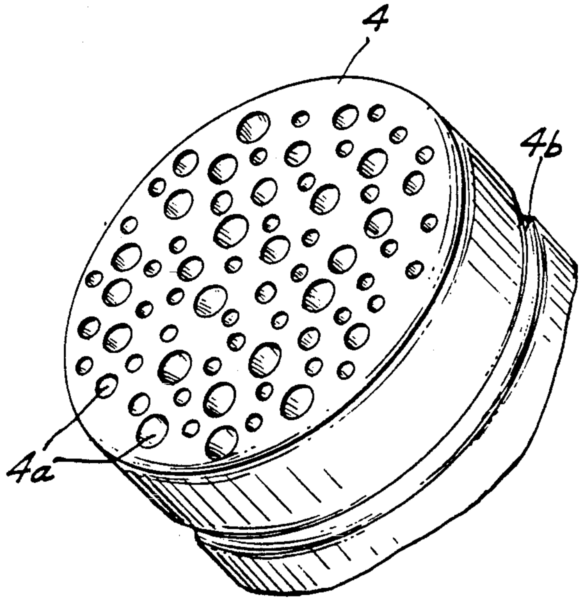
FIG. 6 shows a suction nozzle comprising suction openings of various sizes.
Figure 7A:
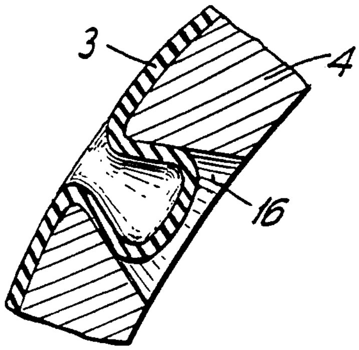
FIG. 7*a* shows a suction opening with a cross section which widens toward the inside.
Figure 7B:
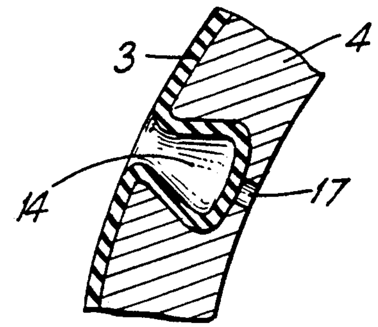
FIG. 7*b* shows a chamber-shaped suction opening.
Figure 8:
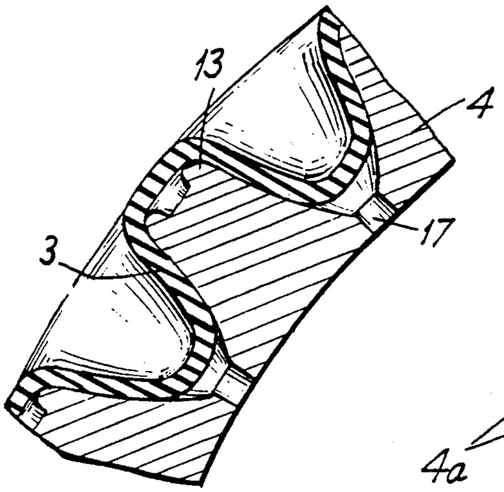
FIG. 8 shows a suction opening with a projecting bead.
Figure 9:
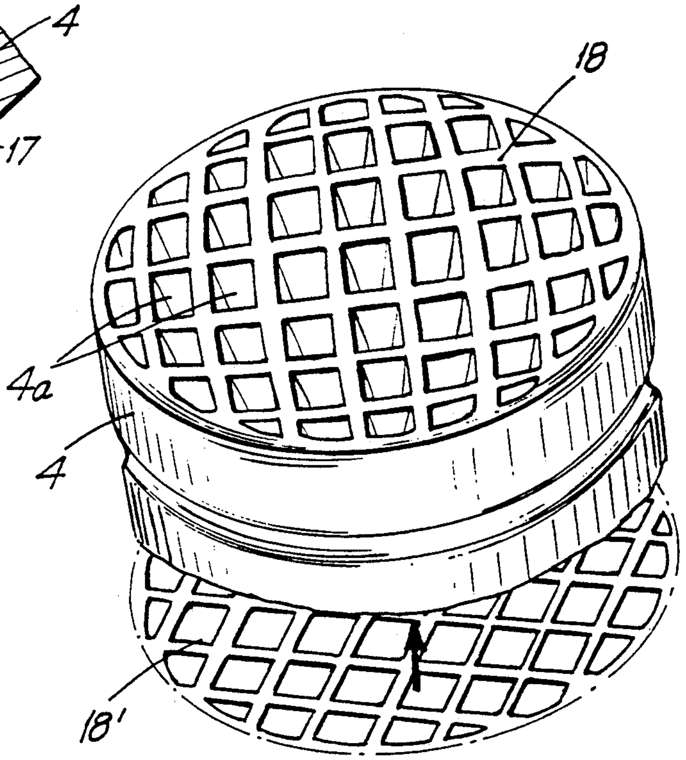
FIG. 9 shows a construction of the suction opening by means of offset grids.

The free suction openings 4*a* not pressed against the skin 6 are closed by the diaphragm 3 so that there is no vacuum loss or only a slight vacuum loss. The suction openings 4*a* are preferably constructed so as to be cone-shaped or chamber-shaped (conical chamber 8, FIG. 3) with a cross section which tapers toward the inside, so as to prevent the rubber diaphragm 3 from being pressed into the free openings to an excessive degree, whereas no vacuum pressure can build up at the other openings pressed against the skin 6. The elastic diaphragm 3 can vary in thickness, preferably having a thickness which increases toward the edge 15 (FIG. 5) and thus ensures a vacuum compensation. As shown in FIG. 7*a*, the suction opening 4*a* can have a cross section which widens toward the interior of the suction nozzle 4 or, as shown in FIG. 7*b*, the suction opening can be in the form of a chamber 14 which comprises a through-hole 17 toward the interior of the suction nozzle 4. FIG. 9 shows the construction of the openings 4*a* by means of offset grids 18. The size of the suction openings 4*a* can vary from one opening to the other (FIG. 6) so as to act in an optimal manner on different pore sizes or skin types. The edge of an opening 4*a* can have a projecting bead 13 (FIG. 8) which forms a valve with the diaphragm. This valve has the function of an exhaust valve for the excess quantity of exiting air when the diaphragm 3 is relaxed. Thus, the object of the exhaust valve is similar to that of the lateral venting ducts described previously.

Figure 3:
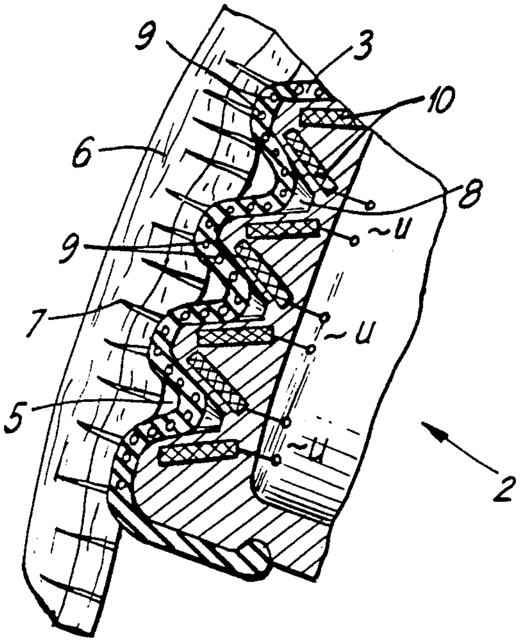
FIG. 3 shows the suction nozzle with a metallized elastic diaphragm and electromagnetic drive.

FIG. 3 shows an embodiment having a metallized elastic diaphragm 9 with an electromagnetic drive 10. The advantages of the magnetic drive consist on the one hand in the independence of the individual secondary mini-vacuum pumps 5 from one another regardless of how many openings 4*a* are pressed against the skin or remain free along the skin, so that the same vacuum action is always achieved, and on the other hand in the freedom of vibration, since no heavy mechanical parts are moved, as well as in the improved frequency response and the improved configuration possibility of the pulse shape. As an additional advantage, it is also worth noting that the electromagnetic drive is maintenance-free and has a long life compared to an electric motor with bar collector, and the massaging action of the elastic diaphragm on the skin is increased as a result of the fine magnet inserts 9.

Figure 4:
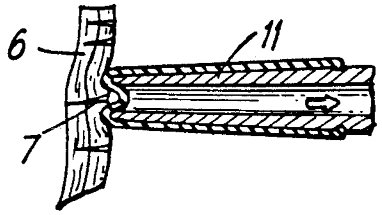
FIG. 4 shows a narrow suction tube for high vacuum values.

FIG. 4 illustrates an embodiment of a device specifically suited for the treatment of individual pimples and blackheads, wherein the narrow suction tube 11 allows aimed placement and makes it possible to build up higher vacuum values.

The skin-cleaning action of the suggested technical solution is reinforced by the use of cosmetic compositions, wherein grease substances help to loosen the skin deposits and seal the suction openings placed against the skin. In so doing, a skin-care effect is also achieved in that, on the one hand, a massage is carried out which is gentle and simultaneously penetrates into the skin and stimulates the blood circulation in the skin layers and thus provides for an improved supply of nutrients and moisture to the skin cells. On the other hand, the utilized substances are simultaneously massaged into the deeper skin layers. A combination with steam treatment, as is conventional in cosmetic salons, further increases the cleaning action as is to be expected.

While the invention has been illustrated and described as embodied in a suction device for cleaning the skin, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims.

What is claimed is:

1. A suction device for cleaning skin comprising:

a suction nozzle having a plurality of openings;
an elastic diaphragm which covers the openings; and
means for generating a pulsating driving force for drawing the elastic diaphragm into the openings so that the diaphragm forms a plurality of pulsating secondary vacuum pumps in contact with the skin, wherein the pulsating drive force generating means further comprises electromagnets for generating the pulsating drive force and the diaphragm further comprises one of fine inserts and a layer of magnetic material.

2. The suction device of claim 1, wherein the openings are formed by a plurality of offset grid means.

3. The suction device of claim 1, wherein each opening has an inwardly widening cross-section.

4. The suction device of claim 1, wherein each opening has a projecting bead at an end thereof.

5. The suction device of claim 1, wherein the suction nozzle has a convex end surface, and the diaphragm engages substantially the entire end surface of the suction nozzle.

6. A suction device for cleaning skin comprising:
a suction nozzle having a plurality of openings;
an elastic diaphragm which covers the openings; and
means for generating a pulsating driving force for drawing the elastic diaphragm into the openings so that the diaphragm forms a plurality of pulsating secondary vacuum pumps in contact with the skin, wherein the pulsating drive force has variable pulse parameters including amplitude, pulse repetition frequency and mark space ratios.

7. The suction device of claim 6, wherein the openings are formed by a plurality of offset grid means.

8. The suction device of claim 6, wherein each opening has an inwardly widening cross-section.

9. The suction device of claim 6, wherein each opening has a projecting bead at an end thereof.

10. The suction device of claim 6, wherein the suction nozzle has a convex end surface, and the diaphragm engages substantially the entire end surface of the suction nozzle.

11. A suction device for cleaning skin comprising:
a suction nozzle having a plurality of openings;
an elastic diaphragm which covers the openings, wherein the thickness of the diaphragm increases toward an edge of the diaphragm; and
means for generating a pulsating driving force for drawing the elastic diaphragm into the openings so that the diaphragm forms a plurality of pulsating secondary vacuum pumps in contact with the skin.

12. The suction device of claim 11, wherein the openings are formed by a plurality of offset grid means.

13. The suction device of claim 11, wherein each opening has an inwardly widening cross-section.

14. The suction device of claim 11, wherein each opening has a projecting bead at an end thereof.

15. The suction device of claim 11, wherein the suction nozzle has a convex end surface, and the diaphragm engages substantially the entire end surface of the suction nozzle.

* * * * *